United States Patent [19]

Riley

[11] Patent Number: 4,579,003
[45] Date of Patent: Apr. 1, 1986

[54] INSTRUMENT FOR TESTING EARTHEN SAMPLES UNDER TRIAXIAL LOAD CONDITIONS

[76] Inventor: Brodie D. Riley, 2640 Dundee Rd., San Pablo, Calif. 94806

[21] Appl. No.: 693,153

[22] Filed: Jan. 22, 1985

[51] Int. Cl.$^4$ .......................... G01N 3/00; G01N 3/08
[52] U.S. Cl. .......................... 73/784; 73/794; 73/807
[58] Field of Search ............. 73/784, 794, 795, 807

[56] References Cited

U.S. PATENT DOCUMENTS

| | | | |
|---|---|---|---|
| 3,199,341 | 8/1965 | Heuer et al. | 73/807 |
| 3,505,860 | 4/1970 | Bishop et al. | 73/807 |
| 3,580,334 | 5/1971 | Broussard et al. | 73/784 |
| 3,975,950 | 8/1976 | Erdei | 73/795 |
| 4,149,407 | 4/1979 | Strom et al. | 73/794 |

*Primary Examiner*—Anthony V. Ciarlante
*Attorney, Agent, or Firm*—Harris Zimmerman; Howard Cohen

[57] ABSTRACT

An instrument for testing earthen samples under triaxial load conditions includes an upwardly extending cylindrical housing with two access windows formed in the side thereof, and a transparent cylindrical sleeve adapted to be slidably received about the housing to seal the chamber within. A lower stage is supported on a laterally translatable bearing block, and connected to a double-acting horizontal hydraulic ram. An upper stage is disposed in superjacent opposition to the lower stage, and is connected to the lower end of a vertical hydraulic ram supported atop the housing. The stages include shallow sockets adapted to receive sample platens in vertical alignment with the vertical ram. The platens each include peripheral grooves adapted to be engaged by swing clamps extending from each stage. Each platen includes a filter stone portion adapted to contact a core sample disposed between the platens, with a fluid channel extending radially through each platen to the filter stone. The platens are assembled with the core sample therebetween, and a sleeve membrane is secured thereabout with O-rings. The sample assembly is evacuated, locked to the stages with the swing clamps, and connected through the fluid channels to a water source to saturate the samples. The sample is then compressively loaded by the vertical ram and cyclically driven by the horizontal ram to simulate triaxial loading. LVDT sensors measure strain in both axes to determine soil properties under actual load conditions.

23 Claims, 10 Drawing Figures

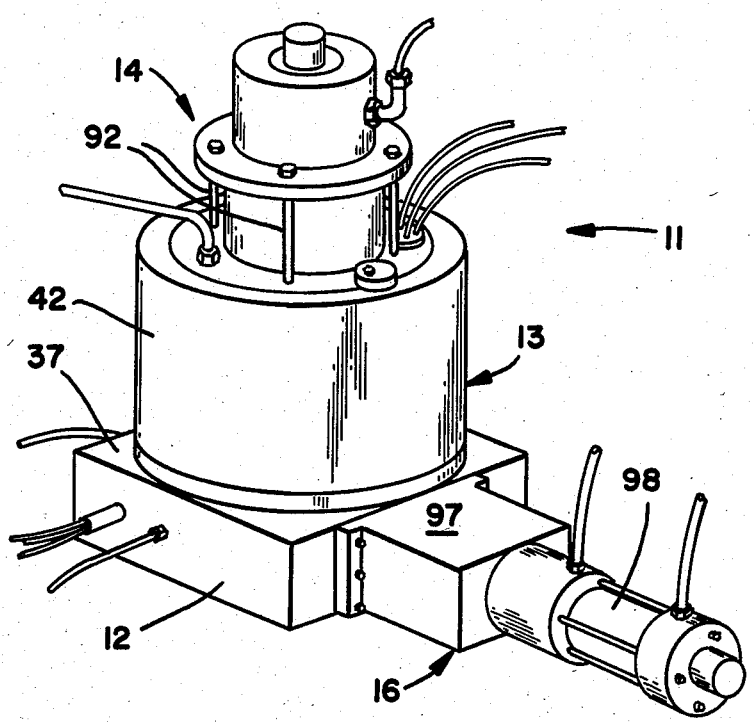
FIG _ 1
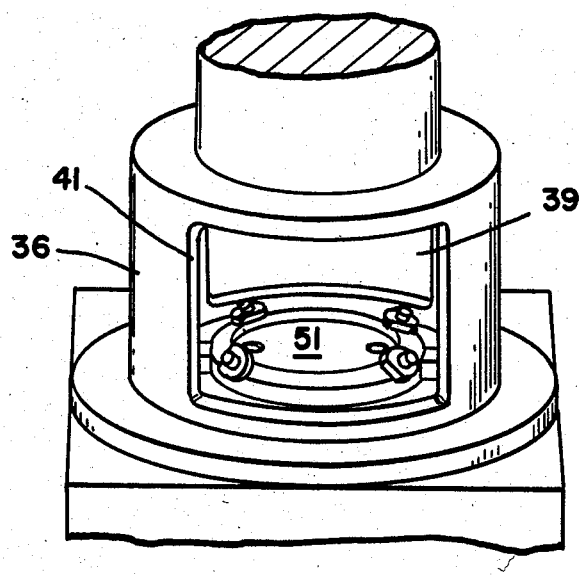
FIG _ 2

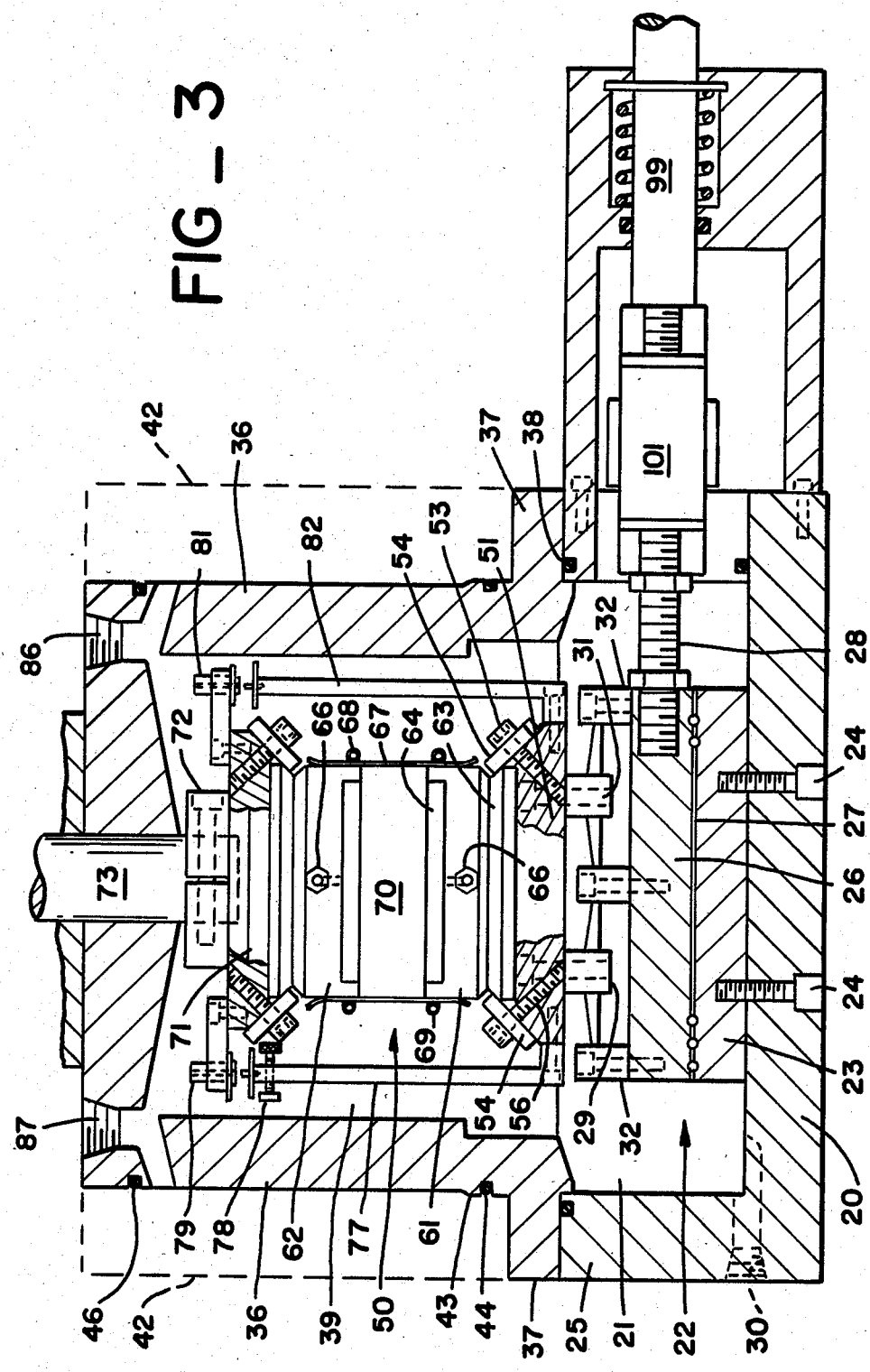

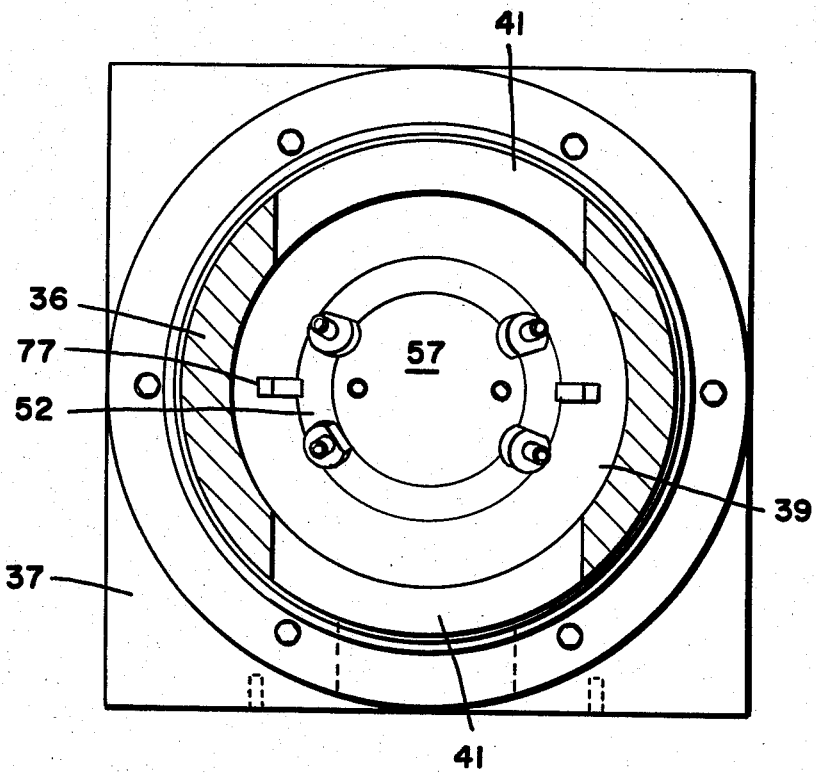
FIG _ 4
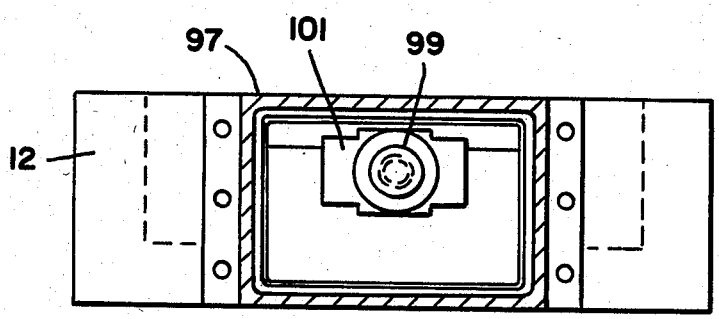
FIG _ 5

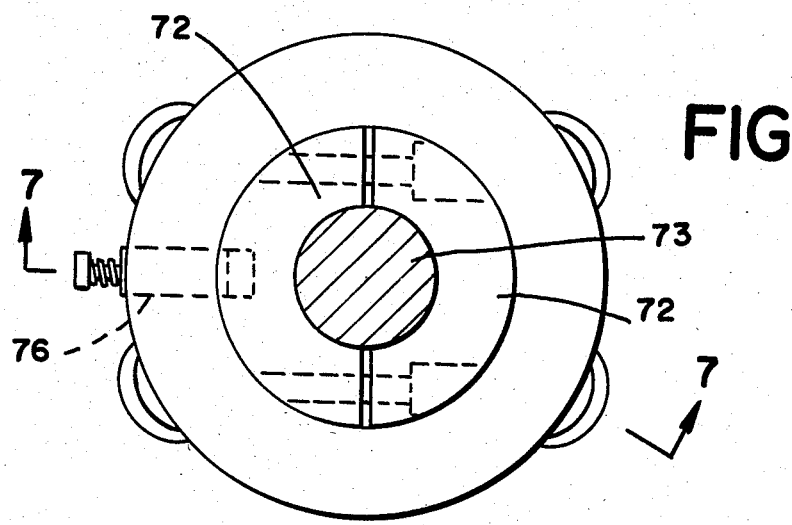
FIG_6
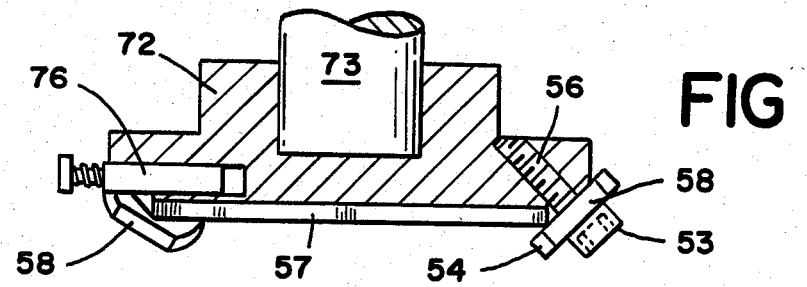
FIG_7
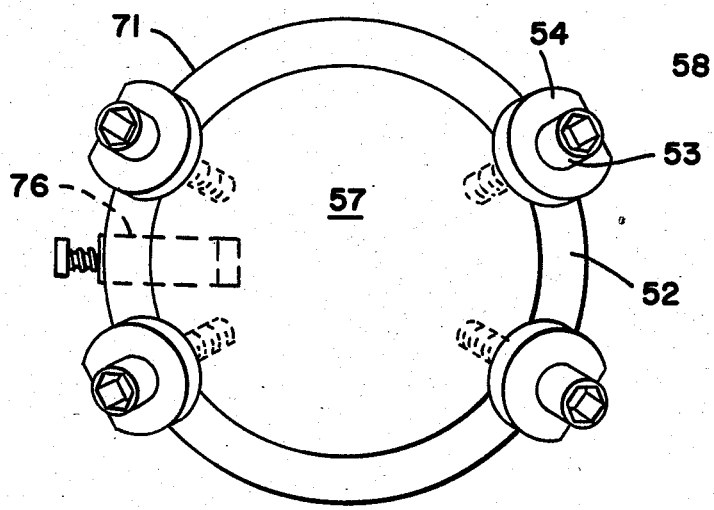
FIG_8

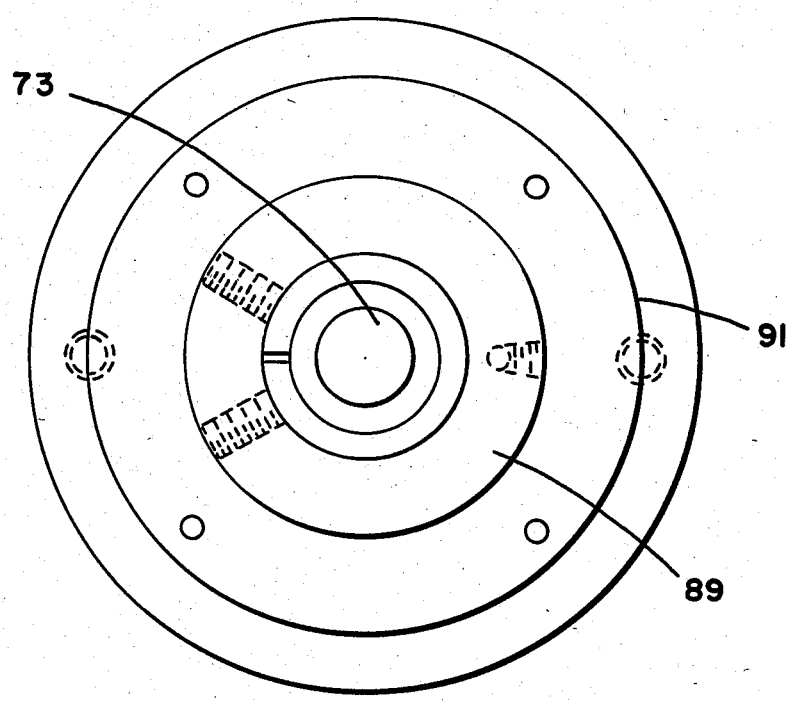
FIG_9
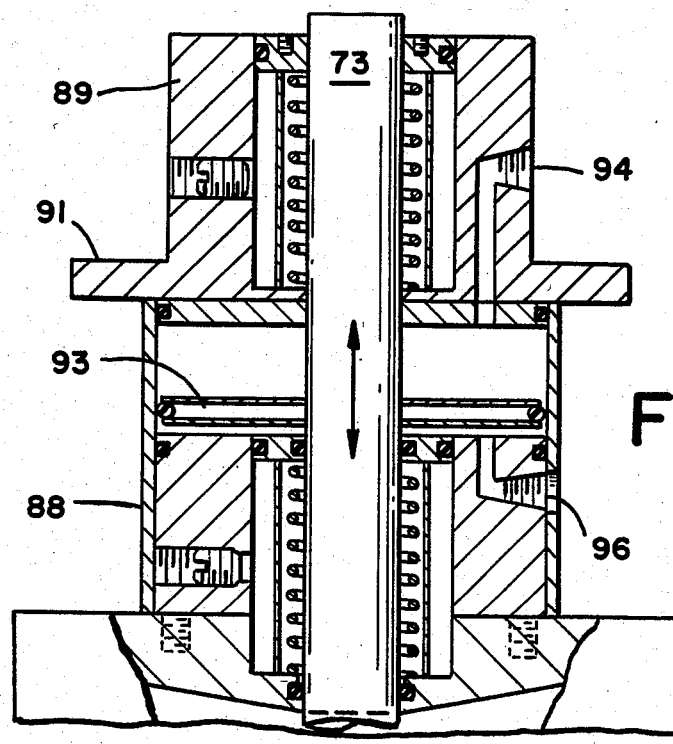
FIG_10

INSTRUMENT FOR TESTING EARTHEN SAMPLES UNDER TRIAXIAL LOAD CONDITIONS

BACKGROUND OF THE INVENTION

In the siting and planning of large scale construction projects, such as dams, buildings, offshore drilling platforms, nuclear power plants, and the like, it is necessary to ascertain the nature and strength of the earthen formation which will support the construction project. Typically, core samples of the subsurface earthen formation are obtained, and subjected to testing to discover critically important factors such as yield strength, ambient stress patterns, elasticity, plasticity, etc., of the earth at the potential construction site. These factors are generally determined through the use of instruments known in the prior art. Such instruments generally operate by subjecting the core sample to an axial compressive load while measuring the strain created by the load, the load factor being increased until the sample fails. This form of test is generally reliable in determining the strength of the subsoil formation under the static load of the project to be built.

However, in many siting situations the dynamic situation is not static, but is subject to rapidly varying load factors. This may occur in earthquake zones, where rapid lateral acceleration not only alters the vertical equilibrium, but also may significantly change the strength of the subsoil formation. Likewise, offshore platforms are subject to wave action creating an added lateral force vector which varies greatly in direction and magnitude. These lateral forces must be taken into account when a construction project is planned to assure the survival of the project.

There is a deficiency in the prior art in instruments which can test subsoil samples in dynamically varying conditions as well as static load conditions. Prior art instruments have tended to introduce large errors into the test results, due in part to poor mounting of the sample which results in erroneous strain measurements. A further problem in the presence of excessive friction in the mounting of the sample for lateral loading in addition to axial compression. The frictional effects results in data which is open to question and is often not reproducible in successive tests. When the data is not reliable it is dangerous to use it to make decisions involving expensive and large scale projects.

Furthermore, the prior art instruments are deficient in that they require a great amount of time to prepare and mount each sample in the instrument. Thus each testing procedure may require a long time, and the testing of a large number of core samples may be prohibitively lengthy and costly. Also, the preparation may necessitate rehydration of the sample, and this task has proven to be problematical in prior art setups.

SUMMARY OF THE PRESENT INVENTION

The present invention generally comprises a test instrument for determining the properties and characteristics of core samples and the like under realistic load conditions involving varying combinations of vertical and lateral stresses. Its most salient feature is that it provides accurate data which is reproducible in repeated tests, and that the data forms a reliable basis for making a realistic appraisal of underground formations.

The instrument is designed for testing earthen samples under triaxial load conditions, and includes an upwardly extending cylindrical housng with two access windows formed in the side thereof. A transparent cylindrical sleeve is adapted to be slidably received about the housing to seal the chamber within, the sleeve retaining fluid under pressure in the chamber. A lower stage is supported on a laterally translatable bearing block, and connected to a double-acting, horizontally disposed hydraulic ram. An upper stage is disposed in superjacent opposition to the lower stage, and is connected to the lower end of a vertical hydraulic ram supported atop the housing. The stages include shallow sockets adapted to receive sample platens in vertical alignment with the vertical ram.

The platens each include peripheral grooves adapted to be engaged by swing clamps pivotally supported at the sides of each stage. Each platen includes a filter stone portion adapted to contact a core sample disposed between the platens, with a fluid channel extending radialy through each platen to the filter stone. The platens are assembled with the core sample therebetween, and a sleeve membrane is secured thereabout with O-rings. The sample assembly is then evacuated, locked to the stages with the swing clamps, and connected through the fluid channels to a water source to saturate the samples. The sample is then compressively loaded by the vertical ram and cyclically driven by the horizontal ram to simulate triaxial loading. LVDT sensors measure strain in both axes to determine soil properties under actual load conditions, and load cells under the lower stage measure the actual stresses applied to the sample in both the lateral and vertical directions.

Each sample may be assembled to platens with a sleeve membrane and evacuated prior to positioning the assembly in the chamber of the instrument. Thus the actual testing procedure is run much more quickly, and a number of tests on different core samples may be run rapidly.

BRIEF DESCRIPTION OF THE DRAWING

FIG. 1 is a perspective view of the test instrument of the present invention.

FIG. 2 is a perspective view of the test chamber of the instrument of the present invention.

FIG. 3 is a cross-sectional elevation of the test instrument of the present invention.

FIG. 4 is a lateral cross-sectional view of the test chamber of the instrument of the present invention.

FIG. 5 is a cross-sectional elevation of the base portion of the instrument of the present invention.

FIG. 6 is a lateral partial cross-sectional view of the upper stage assembly of the present invention.

FIG. 7 is a cross-sectional elevation of the upper stage assembly, taken along line 7—7 of FIG. 6.

FIG. 8 is a bottom view of the upper stage assembly.

FIG. 9 is a top view of the upper vertical drive assembly of the pressent invention.

FIG. 10 is a cross-sectional elevation of the portion of the present invention depicted in FIG. 9.

DESCRIPTION OF THE PREFERRED EMBODIMENT

The present invention generally comprises a testing instrument for determining the properties of earthen samples under independently varied, triaxial load conditions. The most salient features of the invention is that it produces accurate data that is reproducible in repeated tests, and that it is designed to permit rapid testing of a plurality of earthen samples.

With reference to FIG. 1, the test instrument 11 generally includes a base assembly 12 adapted to be supported on a firm surface, and a test chamber assembly 13 disposed atop the base assembly. A vertical hydraulic cylinder assembly 14 is disposed atop the test chamber assembly 13, and a horizontal hydraulic cylinder assembly 16 is secured to one side of the base assembly 12 below the test chamber assembly.

The base assembly 12, also depicted in FIG. 3, comprises a generally rectangular member having a centrally disposed, upwardly opening coffer 21 defined therein. The coffer 21 is defined by a rectangular base panel 20 and sidewalls 25 extending upwardly from the edges thereof. A fill and drain port 30 is provided for the coffer, for reasons explained in the following description. A bearing block assembly 22 is supported on a medial portion of the panel 20 and secured rigidly thereto by bolts 24. The bearing block assembly includes a fixed lower block 24 into which the bolts 24 are threaded, and a translating upper block 26. Disposed between the two blocks are a plurality of roller bearings 27 which permit lateral translation of the upper block with a minimum of frictional resistance. A lateral drive shaft is threaded into the upper block 26 to drive the latter with a static or cyclically varying force, as will be explained in the following description.

Extending upwardly from the top surface of the upper block 26 are a plurality of posts 32 secured rigidly to the upper block in tapped holes therein. A pair of solid state load measuring cells 29 and 31 are suspended between the posts 32 with their upper, load sensitive surfaces disposed generally coextensively with the upper opening of the coffer 21. Many solid state load cells are known in the prior art, and any may be chosen so that both of the cells measures the vertical load on the upper bearing block. The readings may be averaged to accurately determine the actual load applied.

The test chamber assembly 13, which is supported atop the base assembly 12, includes a generally cylindrical housing 36 having a vertically disposed axis of symmetry. A flange 37 extends radially outwardly from the lower end portion of the housing 36. The rectangular configuration of the flange 37 is dimensioned to be joined to the sidewalls 25 of the base 12. An O-ring seal 38 disposed in the upper edge portions of the sidewalls 25 forms a continuous pressure seal between the housing 36 and the base 12. The housing 36 is hollow, having an interior test chamber 39 which is in open flow communication with the coffer 21.

A significant feature of the present invention is the provision of a pair of diametrically opposed window openings 41 in the sidewall of the cylindrical housing 36. The window openings comprise rectangular openings extending a substantial portion of the height of the housing and each describing an angle of approximately 90° to 100°. The windows provide easy access to the test chamber 39, while the remaining portions of the cylindrical sidewall have sufficient curvature to retain substantial rigidity and strength.

The test chamber assembly 13 also includes a generally cylindrical sleeve 42 which is provided to seal the window openings 41. The sleeve 42 comprises a generally cylindrical, hollow tubular section of relatively thick, transparent plastic such as Lucite or the like which permits direct viewing of the sample being tested within the chamber 39. The housing 36 is provided with a slight flange 43 extending outwardly from the lower end thereof, and the sleeve 42 is formed in complementary fashion with a slight counterbore extending axially in the lower end thereof. The sleeve 42 is dimensioned to be received about the housing 36 with minimal clearance to permit translation of the sleeve thereabout with slight manual effort. Thus with slight effort and a few seconds time a technician can open and gain access to the test chamber or close and completely seal the test chamber. This convenience has not been found in prior art instruments. An O-ring seal 44 extends about the flange 43, while an O-ring seal 46 extends about the upper end of the housing 36. The sleeve 42 contacts the seals 44 and 46 continuously about the housing 36 to retain fluid under pressure in the chamber 39. It may be appreciated that the concentricity of the sleeve 42 also aids in strengthening the cylindrical housing 36 in containing the hydrostatic pressure therein, proviing an assembly superior in strength and rigidity and ease of access.

Disposed within the chamber 39 is a sample assembly 50, which includes the earthen sample to be tested. The sample assembly is freestanding, in that it is spaced inwardly from the sidewall of the housing 36, and is independent of the base assembly. Thus the sample assembly is entirely free of frictional interference from the testing instrument itself. The sample assembly includes a lower stage member 51, comprising a disc-like block disposed centrally in the chamber 39 and secured rigidly only to the load cells 29 and 31. The peripheral surface 52 of the lower stage is chamberred to a substantial degree, tapering upwardly to an shallow circular socket 57 disposed in the upper end surface of the stage 51. A plurality of threaded rods 56 extend outwardly from the chamfer surface 52, and are disposed generally perpendicular to the surface 52. Joined to each of the rods 56 is a clamping disc 54, with a nut 53 joined at the distal end to secure the assembly. Each disc 54 is provided with a chordally sheared surface 58 (FIGS. 6–8), so that the center of gravity of each disc is located eccentrically with respect to the axis of the assembly and diametrically opposed with respect to the surface 58. As a result the disc, when the nuts are loosened, will tend to rotate so that the center of gravity is lowest and the chordal surfaces are uppermost.

The sample assembly 50 also includes a pair of lower and upper platens 61 and 62 which are adapted to secure the earthen sample or core sample 70 therebetween. Indeed, the two platens and the core sample comprise a separate assembly which is easily joined or broken down, and which is placed in the test instrument as an integral unit. Each platen includes one end which is dimensioned to be received in one of the sockets 57 with minimal clearance, and an external circumferential V-shaped groove 63 disposed adjacent to the same end of the platen. The groove surface proximate to the adjacent end is inclined at approximately the same angle as the chamfer surface 52, so that the clamping discs 54 may engage the surface 52 and the proximate groove surface at the same time. It may be appreciated that the compressive forces of the nuts 53 acting on the discs 54 and exerted obliquely downwardly on the respective platen are more than sufficient to prevent lateral shifting of the platens relative to the respective stages as well as vertical separation of the platens and stages. Furthermore, this rigid structure is easily disassembled by a few turns of the nuts 53, so that testing procedures are expedited.

The other end surface of each of the platens 61 and 62 are provided with a disc-like insert 64 disposed flush with the end surface and centered about the axis of the assembly 50. The insert 64 comprises a porous material such as a porous natural mineral or a sintered porous metal product. A liquid channel 66 extends radially into each platen, and is joined in flow communication with the medial portion of the porous insert 64. The outer end of the channel 66 is provided with a tapped connector to receive a valve, tubing connector, or the like, for reasons to be described below.

The platens 61 and 62 are dimensioned to approximate the same diameter as the core sample 70. A resilient sleeve 67 of rubber or other elastomeric material is secured about the two platens with the sample 70 therebetween. This step is intended to be taken outside of the instrument, so that the sleeve 67 secures the platens to the sample. A pair of resilient rings 68 and 69 are secured about the sleeve 67 over the opposed platens to retain the sleeve and form a pressure seal. The channels 66 are then connected to a vacuum source, and the sample assembly is evacuated. Ambient external pressure on the outer ends of the platens causes the assembly to be compressed together, while the sleeve 67 and the rings 68 and 69 retain the partial vacuum within the sample, the porous inserts 64, and the channels 66. The channels are then sealed by valves or plugs, and the sample assembly 50 is ready to be mounted in the test instrument.

The upper platen 62 is secured to and supported by an upper stage member 71. The member 71 includes many of the features of the lower stage 51, including the socket 57, the chamfer surface 52, and the plurality of clamping assemblies 53, 54, and 56. All of these components function as described in the foregoing, and need not be detailed again. With reference to FIGS. 6-8, a counterbored socket formed in the upper end of the upper stage is dimensioned to receive the lower end of a vertical drive shaft 73. The upper surface of the upper stage is provided with a split ring clamp 72 which is disposed to releasably engage the lower end portion the vertical drive shaft 73. The drive shaft and the upper stage are disposed generally coaxially with the housing 36 and the sample assembly 50.

To test the physical properties of the sample 70, the sample is placed under compressive stress by force applied through the vertical drive shaft 73 and under lateral shear by force applied through the lateral drive shaft 28. The resultant deformations (strain) of the sample are measured to determine the stress-strain characteristics of the sample. Measurement of the lateral strain of the sample is performed by an LVDT transducer 76 mounted in the upper stage 71 and extending radially outwardly therefrom. A pair of arms 77 and 82 extend upwardly from the lower stage to a point adjacent to the upper extend of the upper stage. An adjustment screw 78 extending from the upper end of the arm 77 is disposed to impinge on the sensor portion of the LVDT, so that relative movement between the upper and lower stages may be measured with extreme accuracy.

In addition, a pair of LVDT sensors 79 and 81 are secured to the upper stage by means of brackets extending rigidly outwardly therefrom. The sensors are disposed vertically and aligned with the upper ends of the arms 77 and 82. The sensors 79 and 81 detect relative movement in the vertical direction with extreme precision. The two vertical sensors 79 and 81 are disposed in diametrical opposition along the lateral drive axis of the shaft 28. Thus if any shifting of the sample from axial alignment occurs during testing, the readings from the sensors 79 and 81 will differ to some extent. These readings may be resolved to determine the actual vertical strain with insignificant error.

It should be noted that the arms 77 and 82 are spaced radially outwardly from the sample assembly 50, so that there is no frictional interference with the sample being tested. Therefor the strain readings from the sensors 76, 79, and 81 reflect the actual deformation of the sample 50.

The vertical hydraulic cylinder assembly 14 is secured atop the housing 36 and joined to the closed upper end of the housing. A pair of tapped fluid vent ports 86 and 87 extend through the upper end of the housing to the chamber 39. The port 30 in the base is provided to supply liquid under pressure to the chamber 39, with ambient air venting through the ports 86 and 87 to assure complete filling of the chamber with liquid. Thus the sample 70 may be surrounded with hydrostatic pressure indentical to ambient subsurface conditions.

With reference to FIGS. 1-3, 9, and 10, the assembly 14 includes a cylinder 88 and a head assembly 89 joined in axial alignment. The head assembly 89 is provided with a flange 91 extending radially outwardly therefrom. A plurality of long bolts 92 extend from the flange 91 to the upper end of the housing 36 to join compressively the members 36, 88, and 89. Within the cylinder a piston 93 is located, with the vertical drive shaft 73 extending axially through the members 88, 89, and 93. Pneumatic fluid ports 94 and 96 extend to either side of the piston to provide fluid under pressure and drive the piston and shaft 73 down and up, respectively.

The horizontal hydraulic cylinder assembly 16 includes a closed rectangular housing 97 extending from one sidewall 25 of the base 12. A double acting hydraulic cylinder 98 is bolted to the housing 97, with the shaft 99 of the cylinder assembly 98 extending generally coaxially with the drive shaft 28. A lateral load cell 101 joins the shaft 99 to the lateral drive shaft 28, so that the force generated by the cylinder assembly 98 is measured directly as it is conducted to the block 26 and the lower stage 51.

PROCEDURE FOR TESTING SOIL SAMPLES

A core sample 70 is first secured between upper and lower platens 62 and 61, and a sleeve 67 is secured thereabout and retained and sealed with rings 68 and 69. The sample assembly is then evacuated using the channels 66, which are then plugged. Many sample assemblies may be prepared in advance. The cylindrical sleeve door 42 is then raised to gain access to the testing chamber 39, and the sample assembly is introduced through one of the windows 41 and placed upon the lower stage 51. The clamp assemblies 53, 54, and 56 are used to secure the sample assembly rigidly to the lower stage. The vertical hydraulic piston is then actuated under low pressure to descend so that the upper platen may be clamped to the upper stage. The channels 66 are then connected to a source of non-pressurized liquid. The partial vacuum extant in the sample causes the liquid to be drawn into the sample, including the voids, microporosities, and the like. Thus the sample becomes completely saturated, mimicking the natural subsurface conditions without subjecting the sample to pressurized fluid and without any entrained air bubbles.

The LVDT sensors are then adjusted to a zero reading, and the door 42 is moved downwardly to seal the test chamber. Liquid is introduced into the chamber 39 through the port 30, and pressurized to a level corresponding to the isostatic pressure at the depth from which the core sample was taken. The lateral and vertical hydraulic cylinders are then placed under control of a microprocessor, which is programmed to load the sample with cyclically varying combinations of compression and lateral shear. The actual loads (stresses) applied to the sample are measured by the load cells 29, 31, and 101, while the strain created in the sample is detected by the sensors 76, 79, and 81. The stress-strain readings are recorded by the microprocessor, as well as failure events and the like. Within a few minutes the entire testing procedure may be completed. The hydraulic pistons are then retracted, the testing chamber is drained through port 30, and the cylindrical door 42 is opened. The sample assembly is removed, and a new one is placed on the lower stage. The testing procedure is then reiterated.

I claim:

1. An instrument for testing earthen samples under triaxial load conditions, comprising; cylindrical housing means having a sealable testing chamber disposed therein, at least one window opening in said housing means to provide access to said testing chamber, a cylindrical sleeve adapted to be removably secured about said housing means and to seal said window opening; base means for supporting said housing means, bearing block means supported on said base means; earthen sample assembly means disposed in said testing chamber; load cell means secured on said bearing block means and supporting said earthen sample means; vertical drive means impinging on one end of said earthen sample assembly means and driving the latter toward said load cell means; lateral drive means connected to said bearing block means to apply lateral shear forces to said earthen sample assembly means, and sensor means for measuring the deformation caused by said vertical and lateral drive means.

2. The instrument of claim 1, wherein said earthen sample means includes an upper and a lower platen disposed in paired, vertically opposed relationship.

3. The instrument of claim 2, wherein said cylindrical housing means and said cylindrical sleeve means are disposed concentrically about a common axis.

4. The instrument of claim 3, further including an upper and a lower stage disposed in paired, vertically opposed relationship, and clamping means for releasably securing the respective upper and lower platen.

5. The instrument of claim 4, wherein each of said stages include a socket formed therein and adapted to receive the respective upper and lower platen, said sockets extending axially with respect to said common axis.

6. The instrument of claim 5, wherein said clamping means includes a plurality of threaded rods extending from each of said stages, a plurality of clamping discs, each slidably received on one of said threaded rods, and a plurality of nuts, each secured to one of threaded rods and impinging on the respective clamping disc.

7. The instrument of claim 6, wherein each of said stages includes an annular, chamferred surface extending thereabout, said threaded rods extending outwardly from said chamferred surface.

8. The instrument of claim 6, further including a pair of annular grooves, each circumscribing one of said platens adjacent to the end thereof received in said socket, each of said annular grooves including an oblique surface adapted to be engaged by said clamping discs, whereby said discs may compressively engage both said oblique surface on said platens and said chamferred surface on said stages to secure the respective platen rigidly and releasably.

9. The instrument of claim 2, wherein each of said platens includes a sample engaging surface, and a pair of porous inserts, each inset in one of said sample engaging surfaces.

10. The instrument of claim 9, further including a pair of fluid channels, each disposed in one of said platens and extending from the exterior thereof to an inner portion of said respective porous insert.

11. The instrument of claim 10, further including a resilient, elastomeric sleeve adapted to be secured about said platens with an earthen sample disposed therebetween.

12. The instrument of claim 11, further including ring means for securing said elastomeric sleeve to said platens and forming a pressure seal therebetween.

13. The instrument of claim 1, wherein said sensor means includes a plurality of transducers supported in said test chamber independently of said housing or base means.

14. The instrument of claim 13, including a pair of vertical strain sensors secured to one of said stages, and measuring arms extending rigidly from the other of said stages to close proximity to said vertical strain sensors.

15. The instrument of claim 14, further including a lateral strain sensor extending from said one stage and disposed to be proximate to a portion of one of said measurement arms.

16. The instrument of claim 13, further including a plurality of load cells interposed between said lower stage and said bearing block means, said load cells being oriented to detect both vertical and lateral loads.

17. The instrument of claim 1, wherein said bearing block means includes a fixed block secured to said base means, a translatable upper block secured atop said fixed block, and roller bearings disposed between said blocks to provide free translation of said upper block in the lateral direction.

18. The instrument of claim 17, wherein said base means includes a shallow, upwardly opening coffer in which said bearing block means is disposed.

19. The instrument of claim 18, wherein said coffer is sealed by said cylindrical housing means, said coffer and said testing chamber forming a continuous closed volume.

20. The instrument of claim 19, further including port means extending through said cylindrical housing means and adapted to fill said volume with fluid under pressure.

21. The instrument of claim 1, wherein said vertical drive means includes a double acting hydraulic piston secured atop said cylindrical housing means.

22. The instrument of claim 21, wherein said lateral drive means includes a double acting hydraulic piston secured to one side of said base means.

23. An instrument for testing earthen samples, comprising; cylindrical housing means having a sealable testing chamber disposed therein, at least one window opening in said housing means to provide access to said testing chamber, a cylindrical sleeve adapted to be removably secured about said housing means and to seal said window opening; base means for supporting said housing means, earthen sample assembly means disposed in said testing chamber; load cell means supporting said earthen sample means; means for applying stresses to said earthen sample assembly means along more than one axis, and sensor means for measuring the deformation caused by said stresses.

* * * * *